United States Patent [19]

Marotel et al.

[11] Patent Number: 4,824,585
[45] Date of Patent: Apr. 25, 1989

[54] CALCIUM SOAPS POSSESSING A HIGH BASICITY RESERVE

[75] Inventors: Yves Marotel, Coye la Foret; Francis Hurier, Pont Sainte Maxence; Jean-Louis Mansot, Villefranche/Saone; Jean-Michel Martin, Lozanne, all of France

[73] Assignee: Norsolor, Paris la Defense, France

[21] Appl. No.: 947,716

[22] Filed: Dec. 30, 1986

[30] Foreign Application Priority Data

Dec. 30, 1985 [FR] France ................................ 85 19393

[51] Int. Cl.$^4$ ............................................ C10M 129/38
[52] U.S. Cl. ...................................... 252/39; 252/40.5; 252/40.7; 252/389.61
[58] Field of Search ...................... 252/39, 40.5, 40.7, 252/389.61

[56] References Cited

U.S. PATENT DOCUMENTS

| | | | |
|---|---|---|---|
| 3,372,114 | 3/1968 | Rense | 252/39 |
| 3,554,909 | 1/1971 | Hermant et al. | 252/34.7 |
| 4,179,385 | 12/1979 | Ali et al. | 252/33 |

*Primary Examiner*—Jacqueline V. Howard
*Attorney, Agent, or Firm*—Millen & White

[57] ABSTRACT

Calcium superbase soaps consist essentially of calcium dissolved in at least one oil in the form of carbonate and of salts of acids, the said acids consisting of a mixture or otherwise of saturated organic carboxylic acids containing from 7 to 13 carbon atoms in which the linear acid content is from 0 to 40% by weight, the content of acids branched on carbon 2 is from 0 to 20% by weight and the content of acids which are mono- or polysubstituted on carbon 3 and/or of higher rank is higher than or equal to 46% by weight.

These soaps are used in particular as additives in lubricating oils or as oxidation catalysts.

23 Claims, No Drawings

CALCIUM SOAPS POSSESSING A HIGH BASICITY RESERVE

BACKGROUND OF THE INVENTION

The present invention relates to new calcium soaps possessing a high basicity reserve, more commonly called superbase calcium soaps. These superbase calcium soaps may be used in many applications, especially an anticorrosion additives in lubricants. The present invention also relates to a method for preparing these superbase calcium soaps, as well as to the lubricating compositions containing such superbase calcium soaps.

The most widely known superbase calcium soaps are salts of alkylarylsulphonic acids. These are compounds which are difficult to prepare and to employ. A traditional process for preparing these compounds consists in reacting an alkylarylsulphonic acid with a metal oxide or hydroxide in a mineral oil. The reaction takes place in the presence of carbon dioxide (or $CO_2$) and in the presence of promoters which make the $CO_2$ easier to fix. The promoters are labile hydrogen compounds such as phenols, alcohols and aminoalcohols. When the reaction has ended, a cloudy solution is obtained and is purified by centrifuging or filtration. The precipitate obtained in this manner contains, in particular, acid in the form of salt which is extracted in order to minimize the losses of acid (U.S. Pat. No. 4,225,509). Processes of this kind lead to calcium superbase salts of alkylarylsulphonic acids which have a TBN (or Total Basic Number) greater than or equal to 200, and capable of going up to 350. TBN is intended to define the basicity reserve of a superbase soap. The TBN of a superbase soap is the potassium hydroxide equivalent corresponding to one gram of soap when its basicity is titrated with a strong acid. It is expressed in milligrams of potassium hydroxide per gram of calcium superbase salt. This value is defined in accordance with the ASTM standard D 2896-73. Another major disadvantage of superbase calcium soaps of alkylarylsulphonic acids lies in the fact that they yield cloudy solutions which make them awkward to use.

SUMMARY OF THE INVENTION

New calcium superbase soaps which do not possess the disadvantage of the known superbase soaps have been discovered, which have a high TBN of the order of 400 or even higher, and which yield perfectly stable and clear solutions when employed.

More precisely, the calcium superbase soaps according to the invention are characterized in that they contain calcium dissolved in at least one oil in the form of carbonate and of salts of acids, the said acids consisting of a mixture or otherwise of saturated organic carboxylic acids containing from 7 to 13 carbon atoms, having the following characteristics:

a linear acid content of between 0 and 46% by weight, a content of acids which are branched on carbon 2 of between 0 and 20% by weight, and a content of acids which are mono- or polysubstituted on carbon 3 and/or on the carbons of higher rank, which is equal to or greater than 50% by weight.

Within the meaning of the present invention, oil is understood to mean natural oils, semisynthetic oils and synthetic oils. There may be mentioned, for example, oils of animal or vegetable origin, mineral oils, liquid petroleum oils such as kerosene, gas oil, petroleum spirits, mineral lubricating oils, synthetic lubricating oils such as esters of dicarboxylic acids or polyol esters. It is also possible to use a mixture of natural oils and/or semisynthetic oils and/or synthetic oils which are chosen, for example, from those listed above. Preferably, use is made of liquid oils in which the calcium superbase soaps are used as additives. The calcium superbase soaps according to the invention are concentrates of calcium salts which can be readily mixed with lubricating compositions. The calcium superbase soaps according to the invention contain 5 to 80% by weight of oil. The calcium soaps according to the invention preferably contain 30 to 60% by weight of oil, in order to have the benefit, at the same time, of a calcium soap with a high alkalinity reserve and of a completely transportable product.

The calcium superbase soaps are preferably prepared from saturated $C_8$, $C_9$ and $C_{10}$ organic carboxylic acids which consist of isomeric mixtures and which are generally known as oxo acids. These oxo acids are characterized by a low linear acid content, generally less than or equal to 10% by weight, a low content of acids which are branched on carbon 2, generally less than or equal to 10% by weight, and a high content of acids which are mono- or polysubstituted on carbon 3 and/or carbons of higher rank, which is generally greater than 80% by weight. The oxo acids are obtained by hydroformylation of $C_7$, $C_8$ and $C_9$ olefins, followed by an oxidation.

Still more preferably, the calcium soaps according to the invention are prepared from the $C_8$ saturated carboxylic acid (that is containing 8 carbon atoms) marketed under the trademark Cekanoic, this acid consisting of an isomeric mixture of octanoic acids containing at most 10% by weight of n-octanoic acid, at most 10% by weight of $C_8$ acids which are branched on carbon 2 and at least 80% by weight of $C_8$ acids which are branched on carbon 3 and/or the carbons of higher rank. In fact, it has surprisingly been found that the use of this acid makes it possible to obtain calcium soaps with a very high basicity of the order of 500 or higher.

Among the organic carboxylic acids which are also suitable for the present invention there may also be added the derivatives which are mono- or polysubstituted in the 3-position and/or of higher rank of the acids corresponding to heptanoic acid, octanoic acid, nonanoic acid, decanoic acid, undecanoic acid and dodecanoic acid. These include, for example, 3-methylhexanoic acid, isooctanoic acid, 4,5-dimethylhexanoic acid, isononanoic acid, 3,5,5-trimethylhexanoic acid, isodecanoic acid, 3-ethyloctanoic acid, isoundecanoic acid, 4-ethylnonanoic acid and isododecanoic acid. The mixture of one of more of the abovementioned acids, whether mixed or not with their isomers, is also suitable for the present invention, it being understood that the content of linear acids does not exceed 46% and that the content of acids which are substituted on carbon 2 does not exceed 20%. It has been found, in fact, that the linear acids and that the acids branched on carbon 2 lead to the formation of a viscous product, or to a setting solid or, alternatively, to a precipitate which renders the product practically useless.

The present invention also relates to a process for the preparation of the calcium superbase soaps described above, according to which a calcium oxide and/or hydroxide is reacted, with stirring, with carbon dioxide (or $CO_2$) which is bubbled through the reaction mixture and at least one organic carboxylic acid, in the presence of at least one promoter which makes $CO_2$ fixation easier and at least one catalyst, and in that the water formed during the reaction is removed. The process according to the invention is characterized in that the reaction is performed in at least one organic solvent at a temperature of between 80° and 120° C., and in that the said acid is a saturated organic carboxylic acid containing from 7 to 13 carbon atoms, in which the content of linear acids is less than or equal to 40% by weight, in which the content of acids branched on carbon 2 is less than or equal to 20% by weight, and in which the content of acids branched on carbon 3 and/or the carbons of higher rank is equal to or higher than 40% by weight.

When the reaction has ended, after filtration, the organic solvent is replaced by an oil, or a mixture of oils, chosen from natural oils and/or semisynthetic ois and/or synthetic oils. However, the oil chosen is preferably that which forms the basis of the lubricating composition to which the calcium superbase soap is added.

In accordance with a preferred embodiment of the process according to the invention, the organic solvent is allowed to evaporate during the reaction and is recycled into the reaction mixture so as to produce therein a bubbling action which promotes the reaction.

At least one nonpolar organic solvent chosen from naphtha, hexane, kerosene, benzene, toluene or xylene is used among the organic solvents which can be used in the process according to the invention. It is also possible to use a mixture of paraffinic hydrocarbons of mineral or synthetic origin, preferably containing a low proportion of aromatic and/or naphthenic hydrocarbons, such as white spirit. It is also possible to consider the use of polar organic solvents such as alcohols, for example 1-butanol, 2-butanol, ethylene glycol, propylene glycol, ethylene glycol monomethyl ether, ethylene glycol dimethyl ether, diethylene glycol and its ethers, mixtures of alcohols derived from paraffin, or methyl ethyl ketone.

The molar ratio of calcium to the organic carboxylic acid employed in the reaction is generally between 0.55 and 2, which corresponds to a basicity of between 1.1 and 4.

It should be recalled that the basicity is equal to the ratio of equivalents of calcium to the equivalents of carboxylic acids which are employed, that is to say, to the molar ratio of the calcium concentration to that of the carboxylic acids, multiplied by 2.

Furthermore, an hourly flow rate of carbon dioxide is imposed such that the hourly mass ratio of carbon dioxide to calcium is between 0.5 and 2, and preferably between 0.7 and 1.5.

Among the catalysts which may be used in the process according to the invention there may be mentioned metal oxides, for example zinc oxide, aluminum oxide $Al_2O_3$, silver oxide $Ag_2O$, magnesium oxide MgO, and zinc carboxylates such as zinc octanoate.

Among the promoters which make $CO_2$ fixation easier and which can be used in the present invention there may be mentioned labile hydrogen compounds such as alcohols, for example methanol, 2-propanol, octyl, alcohol, ethylene glycol, triethylene glycol, stearyl alcohol, cyclohexylene glycol alcohol, cyclohexyl alcohol, aromatic alcohols such as phenol; amines, for example aniline, phenylenediamine, or dodecylamine; or, yet again, a mixture of alcohols and/or amines, for example of methanol and aqueous ammonia.

However, preferably, the material used is methanol, which gives the highest basicities and the shortest filtration times during the preparation of the calcium soap according to the invention.

In the calcium superbase soaps according to the invention, the promoters ae used in a proportion of 1 to 25% by weight of final calcium salt, and preferably in a proportion of 5 to 15%.

When dissolved in an oil, the calcium superbase soaps according to the invention yield stable and completely clear solutions. In addition, they have a high basicity reserve (or TBN), of the order of 400 or even higher. They find numerous applications, particularly as lubricant additives. They may also be used as oxidation catalysts or intermediates in the synthesis of other lubrication additives.

EXAMPLES

The present invention will be better understood by referring to the nonlimiting examples of the invention which follow.

In the following examples a 100 Neutral, commercial grade paraffinic oil, and a 200 Neutral commercial grade paraffinic oil are used for the preparation of the calcium soap.

The physical characteristics of these two oils are given in the table below.

| Oil | Density at 15° C. | Flammability point (°C.) | Engler viscosity at 50° C. | Absolute viscosity in cSt at 37.8° C. | Solidification point (°C.) | Acid value (mg/KOH/g) |
| --- | --- | --- | --- | --- | --- | --- |
| 100 Neut. | 865 | 200/220 | 2.3 | 20 | −12/−15 | 0.01 |
| 200 Neut. | 870/890 | 210 | 3.3/3.8 | 42 | −12/−15 | 0.05/01 |

EXAMPLE 1

The preparation of the calcium superbase soap is carried out in a reactor fitted with a mechanical anchor-type stirring system, an electrical heating system and a Dean and Stark distillation apparatus which is connected to a condenser with water separation. This reactor is connected to a device for recycling mainly the organic solvent originating from the condenser, by means of a pneumatic pump, for the purpose of producing in the reaction medium a bubbling action which promotes homogenization. The reactor is also fitted with a carbon dioxide inlet. The following charge (in parts by weight) is introduced into the reactor with mechanical stirring and at atmospheric pressure:

| | |
| --- | --- |
| white spirit: | 286 |
| zinc octanoate (at 10% strength by weight): | 1.2 |
| triethylene glycol: | 35. |

The mixture is heated to 70° C. 128 parts of 97% pure, on a weight basis, calcium hydroxide are then introduced into the reactor and then, after the mixture has been homogenized, 236 parts of isooctanoic acid, which consists of a mixture of isomers containing less than 10% by weight of that branched on the 2-carbon and containing not more than 10% by weight of linear isomer, is gradually run into the reactor.

The reaction is exothermic and the temperature of the mixture reaches 85° C. The temperature of the mixture is then raised to 95° C. and a stream of carbon dioxide is passed through at such a rate that the hourly mass ratio of carbon dioxide to calcium hydroxide is 1.1 for 30 minutes. After the addition of carbon dioxide, the suction pump, which was kept running during the reaction, is stopped. The whole assembly is put under a pressure of $1.33 \ 10^4$ Pa and the temperature in the reactor is raised to 120° C., which enables the residual water present in the reaction mixture to be removed. A total of 29.5 parts of water are removed throughout the reaction. The reaction is then returned to atmospheric pressure and 5 parts of a filtration aid, which is diatomaceous earth in the present case, are added to it. The reaction mixture is then filtered hot (80° C.) at a pressure of $4 \ 10^4$ to $7 \ 10^4$ Pa. 657 parts of calcium salt are obtained, which is in the form of a light-yellow clear solution whose characteristics are as follows:

| | |
|---|---|
| calcium content: | 10.3 |
| basicity (which is equal to 2[Ca]/[acid]): | 2.04 |
| viscosity: | 0.088 pascal second. |

In a second stage, 100 parts of this calcium superbase salt and 14.2 parts of a 200 Neutral paraffinic oil, representing a conventional lubricating base, are introduced into an evaporation system. The white spirit is evaporated off at $1.33 \ 10^3$ Pa and at 110° C. 43.6 parts of white spirit are collected. Finally, 70.6 parts of calcium superbase soap are obtained, this being in the form of an amber-colored transparent solid whose characteristics are as follows:

| | |
|---|---|
| density: | 1.04 g/cm$^3$ |
| dynamic viscosity at 100° C: | 0.5 pascal second |
| total basic number (TBN) (defined according to ASTM standard D 2896-73): | 400 |
| calcium content (in % by weight): | 14.4. |

EXAMPLE 2

Using the procedure described in Example 1, the following charge (in parts by weight):

| | |
|---|---|
| 3,5,5-trimethylhexanoic acid: | 259 |
| calcium hydroxide: | 128 | is reacted with a flow of carbon dioxide such that the hourly mass ratio of carbon dioxide to calcium hydroxide is equal to 1.1, and in the presence of (in parts by weight):

| | |
|---|---|
| triethylene glycol: | 35 |
| zinc octanoate: | 1.2 |
| white spirit: | 263.3. |

29.5 parts of water are recovered during the reaction. When the reaction has ended, 671 parts of calcium superbase salt are collected, this being in the form of a clear light-yellow liquid. In the second stage, which consists in replacing the white spirit present in the calcium superbase salt with an oil which, in this case, is a 200 Neutral paraffinic oil, 8.85 parts of this oil are added to 100 parts of superbase salt. After distillation, there are collected at 120° C. and at $1.33 \ 10^4$ Pa, on the one hand 40 parts of white spirit and, on the other hand, 68.85 parts of calcium superbase salt in the form of an amber-colored solid. Its characteristics are as follows:

| | |
|---|---|
| density: | 1.046 g/cm$^3$ |
| dynamic viscosity at 100° C.: | 4.25 pascal second |
| total Basic Number (TBN): | 381 |
| calcium content (in % by weight): | 13.4. |

EXAMPLE 3

Using the procedure described in Example 1, the following charge (in parts by weight):

| | |
|---|---|
| acid marketed under the trademark Cekanoic CK10, consisting of a mixture of branched isomers of decanoic acid, without branching on carbon 2: | 282 |
| calcium hydroxide: | 128 | is reacted with a flow of carbon dioxide such that the hourly mass ratio of carbon dioxide to calcium hydroxide is equal to 1.1, in the presence of (in parts by weight):

| | |
|---|---|
| triethylene glycol: | 35 |
| white spirit: | 254 |
| zinc octanoate: | 1.2. |

29.5 parts of water are recovered during the reaction. When the reaction has ended, 670.7 parts of calcium superbase salt are collected, this being in the form of a clear light-yellow liquid.

In the second stage, which consists in replacing the white spirit present in the calcium superbase salt with an oil which, in this case, is a 200 Neutral paraffinic oil, 10.2 parts of 200 Neutral oil are added to 100 parts of superbase salt. After distillation at 145° C. at $0.665 \ 10^3$ Pa there are collected, on the one hand, 38 parts of white spirit and, on the other hand, 72.3 parts of calcium superbase salt in the form of an amber-coloured solid. Its characteristics are as follows:

| | |
|---|---|
| density: | 1.046 g/cm$^3$ |
| dynamic viscosity at 100° C.: | 1.25 pascal second |
| TBN: | 376 |
| calcium content (in % by weight): | 13.04 to 13.08. |

EXAMPLE 4

In accordance with the procedure described in Example 1, the following charge (in parts by weight):

| | |
|---|---|
| acid consisting of a mixture of C$_8$, C$_9$ and C$_{10}$ oxo acids containing at most 10% by weight of linear acid, at most 10% by weight of acids branched on carbon 2 and at least 80% by weight of acids branched on carbon 3 and/or of higher rank and whose acid value is equal to 368: | 250 |
| calcium hydroxide: | 128 | is reacted with a flow of carbon dioxide such that the hourly mass ratio of carbon dioxide to calcium hydroxide is 1.1, in the presence of (in parts by weight):

| | |
|---|---|
| triethylene glycol: | 35 |
| zinc octanoate: | 1.2 |
| white spirit: | 287. |

29.6 parts of water are recovered during the reaction. When the reaction has ended, 671.6 parts of calcium superbase salt are collected, this being in the form of a clear light-yellow liquid. In the second stage, 7.1 parts of 200 Neutral trademark paraffinic oil are added to 100 parts of this calcium superbase salt. After distillation at 145° C. and 0.665 $10^3$ Pa, there are collected, on the one hand, 43.1 parts of white spirit and, on the other hand, 64 parts of calcium superbase soaps in the form of an amber-colored liquid. Its characteristics are as follows:

| | |
|---|---|
| density: | 1.1 g/cm$^3$ |
| dynamic viscosity at 100° C.: | 0.58 pascal second |
| TBN: | 399 |
| calcium content (in % by weight): | 14.07. |

EXAMPLE 5 (comparative)

In accordance with the procedure defined in Example 2, the following charge (in parts by weight):

| | |
|---|---|
| linear heptanoic acid: | 260 |
| calcium hydroxide: | 128 | is reacted with a flow of carbon dioxide such that the hourly mass ratio of carbon dioxide to calcium hydroxide is 1.1, in the presence of (in parts by weight):

| | |
|---|---|
| triethylene glycol: | 35 |
| zinc octanoate: | 1.5 |
| white spirit: | 293. |

36 parts of water are recovered during the reaction. When the reaction has ended, 681.5 parts of a very viscous whitish product, which is found to be impossible to filter, are obtained.

EXAMPLE 6 (comparative)

In accordance with the procedure defined in Example 1, the following charge (in parts by weight):

| | |
|---|---|
| a mixture of C$_7$ acids, branched chiefly on carbon 2 and containing 2-ethylpentanoic (60 to 70% by weight) and 2-methylhexanoic (15 to 25% by weight) acids: | 325 |
| calcium hydroxide: | 160 | is reacted with a flow of carbon dioxide such that the hourly mass ratio of carbon dioxide to calcium hydroxide is 1.1, in the presence of (in parts by weight):

| | |
|---|---|
| triethylene glycol: | 41.2 |
| zinc octanoate: | 1.5 |
| white spirit: | 364.2. |

45 parts of water are recovered during the reaction. When the reaction has ended, 846.9 parts of a highly viscous product, which cannot be filtered, are obtained.

EXAMPLE 7 (comparative)

In accordance with the procedure defined in Example 1, the following charge (in parts by weight):

| | |
|---|---|
| 2-ethylhexanoic acid: | 360 |
| calcium hydroxide: | 160 | is reacted with a flow of carbon dioxide such that the hourly mass ratio of carbon dioxide to calcium hydroxide is 1.1, in the presence of (in parts by weight):

| | |
|---|---|
| triethylene glycol: | 41.2 |
| zinc octanoate: | 1.5 |
| white spirit: | 329. |

45 parts of water are recovered during the reaction. When the reaction has ended, 846.7 parts of a viscous reaction mass, which cannot be filtered, are obtained.

EXAMPLE 8 (comparative)

In accordance with the procedure defined in Example 1, the following charge (in parts by weight):

| | |
|---|---|
| 2,2-dimethylhexanoic acid: | 344 |
| calcium hydroxide: | 128 | is reacted with a flow of carbon dioxide such that the hourly mass ratio of carbon dioxide to calcium hydroxide is 1.1, in the presence of (in parts by weight):

| | |
|---|---|
| triethylene glycol: | 35 |
| zinc octanoate: | 1.5 |
| white spirit: | 220. |

36 parts of water are collected during the reaction. When the reaction has ended, 692.2 parts of a viscous reaction mass, which cannot be filtered, are obtained.

EXAMPLE 9

In accordance with the procedure described in Example 1, the following charge (in parts by weight) is reacted:

| | |
|---|---|
| acid marketed under the trademark Cekanoic and consisting of a mixture of isomers of octanoic acid containing at most 10% by weight of linear acid, at most 10% by weight of acids branched on carbon 2 and at least 80% by weight of acids branched on carbons 3 and/or higher rank: | 144 |
| calcium hydroxide: | 95.4 |
| calcium dioxide with a flow such that the hourly mass ratio of carbon dioxide to calcium hydroxide is 1.1, in the presence of (in parts by weight): | |
| methanol: | 100 |
| white spirit: | 261 |
| zinc octanoate: | 1.2. |

101.6 parts of a mixture of water and methanol are recovered during the reaction. When the reaction has ended, 500 parts of calcium superbase salt are collected, this being in the form of a clear light-yellow liquid. In the second stage, 5.1 parts of 200 Neutral paraffinic oil are added to 100 parts of this calcium superbase salt. After distillation at 145° C. at 0.665 $10^3$ Pa, there are collected, on the one hand, 52.2 parts of white spirit and, on the other hand, 51.3 parts of calcium superbase soap in the form of an amber-coloured mass. Its characteristics are as follows:

| | |
|---|---|
| density: | 1.12 g/cm³ |
| dynamic viscosity at 100° C.: | 1.3 pascal second |
| Total Basic Number (TBN): | 502 |
| calcium content (in % by weight): | 17.7 |

EXAMPLE 10 (comparative)

In accordance with the procedure defined in Example 1, the following charge (in parts by weight) is reacted:

| | |
|---|---|
| n-octanoic acid: | 236 |
| calcium hydroxide: | 128 |
| carbon dioxide with a flow such that the hourly mass ratio of carbon dioxide to calcium hydroxide is 1.1, in the presence of (in parts by weight): | |
| triethylene glycol: | 35 |
| white spirit: | 286.3 |
| zinc octanoate: | 1.2 |

Only 13 parts of water are collected during the reaction. When the reaction has ended, 673.5 parts of a viscous mass, which cannot be filtered, are obtained.

EXAMPLE 11 (comparative): (with an acid composition containing 75% of isooctanoic acid and 25% of acid branched on carbon 2)

In accordance with the procedure defined in Example 1, the following charge (in parts by weight):

| | |
|---|---|
| isooctanoic acid: | 108 |
| 2-ethylhexanoic acid: | 36 |
| calcium hydroxide: | 95.4 | is reacted with a flow of carbon dioxide such that the hourly mass ratio of carbon dioxide to calcium hydroxide is 1.1, in the presence of (in parts by weight):

| | |
|---|---|
| methanol: | 59 |
| white spirit: | 277.6 |
| zinc octanoate: | 1.2 |

56 parts of water and methanol are recovered during the reaction. When the reaction has ended, 397.5 parts of a cloudy, yellowish product are obtained. After filtration, the weight of residue on the filter is equal to approximately 25% of the weight of superbase calcium salt.

EXAMPLE 12 (comparative): (with an acid composition containing 50% of straight-chain and 50% of isooctanoic acid)

In accordance with the procedure defined in Example 1, the following charge (in parts by weight):

| | |
|---|---|
| n-octanoic acid: | 72 |
| isooctanoic acid: | 72 |
| calcium hydroxide: | 95.4 | is reacted with a flow of carbon dioxide such that the hourly mass ratio of carbon dioxide to calcium hydroxide is 1.1, in the presence of (in parts by weight):

| | |
|---|---|
| methanol: | 50 |
| white spirit: | 277.6 |
| zinc octanoate: | 1.2 |

63.7 parts of water and methanol are collected during the reaction. When the reaction has ended, 474.2 parts of a cloudy, yellowish liquid product are obtained after filtration, the residue on the filter is equal to approximately 6% by weight of superbase calcium salt.

EXAMPLE 13: (with an acid composition containing 40% of linear and 20% of C-2 branched and 40% of C-3 branched)

In accordance with the procedure described in Example 1, the following charge (in parts by weight) is reacted:

| | |
|---|---|
| n-octanoic acid: | 57.6 (40% by weight of the acid mixture) |
| 2-ethylhexanoic acid: | 28.8 (20% by weight of the acid mixture) |
| 3,5,5-trimethylhexanoic acid: | 57.6 (40% by weight of an acid mixture) |
| calcium hydroxide: | 95.4 |
| carbon dioxide with a flow such that the hourly mass ratio of carbon dioxide to calcium hydroxide is 1.1, in the presence of (in parts by weight): | |
| methanol: | 50 |
| white spirit: | 277.6 |
| zinc octanoate: | 1.2 |

67.3 parts of a mixture of water and methanol are collected during the reaction. When the reaction has ended, 500.9 parts of calcium superbase salt are collected, this being in the form of a clear light-yellow liquid. In the second stage, 65.5 parts of 100 Neutral paraffinic oil are added to 100 parts of this calcium superbase salt. After distillation at 145° C. at 5 mm of mercury there are collected, on the one hand, 55.4 parts of white spirit and, on the other hand, 100 parts of calcium superbase soap in the form of a translucent, amber-colored pasted which can be conveyed at ambient temperature.

The characteristics are as follows:

| | |
|---|---|
| density: | 1.01 g/cm³ |
| dynamic viscosity | |
| at 100° C.: | 0.280 pascal second |
| at 20° C.: | 45 pascal second |
| Total Basic Number (TBN): | 240 |
| calcium content: | 8.5%. |

EXAMPLE 14 (with an acid composition containing 40% of linear and 60% of isooctanoic acid which means that since isooctanoic acid can contain up to 10% of linear octanoic acid that the acid composition can contain up to 46% of linear acid)

Using the procedure described in Example 1, the following charge (in parts by weight) is reacted:

| | |
|---|---|
| n-octanoic acid: | 57.6 |
| isooctanoic acid: | 86.4 |
| calcium hydroxide: | 95.4 |
| carbon dioxide with a flow such that the hourly mass ratio of carbon dioxide to calcium hydroxide is 1.1, in the presence of (in parts by weight): | |
| methanol: | 50 |

| | |
|---|---|
| white spirit: | 277.6 |
| zinc octanoate: | 1.2 |

68 parts of a mixture of water and methaol are recovered during the reaction. When the reaction has ended, 500.2 parts of calcium superbase salt are collected, this being in the form of a clear light-yellow liquid. In the second stage, 13 parts of 200 Neutral paraffinic oil are added to 100 parts of this calcium superbase salt.

After distillation at 145° C. at 5 mm of mercury there are collected, on the one hand, 54.3 parts of white spirit and, on the other hand, 58.7 parts of calcium superbase soap in the form of an amber-colored solid.

The characteristics are as follows:

| | |
|---|---|
| density: | 1.08 g/cm$^3$ |
| dynamic viscosity: at 100° C.: | 1.14 pascal second |
| Total Basic Number (TBN): | 425 |
| calcium content: | 15.1%. |

EXAMPLE 15 (with a composition containing 90% of isooctanoic acid and 10% of acid branched on carbon 2)

In accordance with the procedure described in Example 1, The following charge (in parts by weight) is reacted:

| | |
|---|---|
| isooctanoic acid: | 129.6 |
| 2-ethylhexanoic acid: | 14.4 |
| calcium hydroxide: | 95.4 |
| carbon dioxide with a flow such that the hourly mass ratio of carbon dioxide to calcium hydroxide is 1.1, in the presence of (in parts by weight): | |
| methanol: | 50 |
| white spirit: | 277.6 |
| zinc octanoate: | 1.2 |

68.5 parts of a mixture of water and methanol are recovered during the reaction. When the reaction has ended, 500.2 parts of calcium superbase salt are collected, this being in the form of a clear light-yellow liquid. In the second stage, 16.5 parts of 100 Neutral paraffinic oil are added to 100 parts of this calcium superbase salt.

After distillation at 145° C. at 5 mm of mercury there are collected, on the one hand, 55.4 parts of white spirit and, on the other hand, 61.1 parts of superbase soap in the form of an amber-coloured translucent solid.

Its characteristics are as follows:

| | |
|---|---|
| density: | 1.085 g/cm$^3$ |
| dynamic viscosity: at 100° C.: | 1.35 pascal second |
| Total Basic Number (TBN): | 438 |
| calcium content: | 15.6% |

We claim:

1. A calcium soap having a total basic number of at least on the order of 400, consisting essentially of calcium dissolved in 5–80% by weight of at least one oil, said calcium being in the form of carbonate and of at least one salt of at least one acid, said at least one acid being a saturated hydrocarbyl carboxylic acid containing from 7 to 13 carbon atoms, having the following characteristics:

a linear acid content of 0 to 46% by weight,
   a content of acids branched on carbon 2 of 0 to 20% by weight,
   and a content of acids which are mono- or polysubstituted by alkyl on carbon 3 and/or on carbons of higher rank, of at least 50% by weight, said soap being dissolvable in oil to yield a clear and stable solution.

2. A calcium soap according to claim 1, wherein said at least one hydrocarbyl carboxylic acid is an isomeric mixture of saturated $C_8$, $C_9$ or $C_{10}$ carboxylic acids in which the content of linear acids does not exceed 10% by weight, in which the content of acids branched on carbon 2 does not exceed 10% by weight, and the content of acids branched on carbon 3 and/or the carbons of higher rank is at least 80% by weight.

3. A calcium soap according to claim 1, wherein the at least one hydrocarbyl carboxylic acid is a mixture of isomers of octanoic acid containing at most 10% by weight of n-octanoic acid, at most 10% by weight of acids branched on carbon 2 and at least 80% by weight of acids branched on carbon 3 and/or the carbons of higher rank.

4. A calcium soap according to claim 1, wherein the oil consists essentially of at least one of a natural oil, semisynthetic oil and synthetic oil.

5. In a process for the preparation of calcium superbase soaps comprising reacting calcium oxide and/or hydroxide, while stirring, with carbon dioxide bubbled through the reaction medium and at least one organic carboxylic acid, in the presence of at least one promoter for carbon dioxide fixation and of at least one catalyst, the improvement comprising removing water formed, during the reaction, and conducting the reaction in at least one organic solvent at a temperature of between 80° and 120° C. said acid being a saturated organic carboxylic acid containing 7 to 13 carbon atoms, in which the content of linear acids is less than or equal to 46% by weight, in which the content of acids branched on carbon 2 is less than or equal to 20% by weight and in which the content of acids branched on carbon 3 and/or the carbons of higher rank is equal to or higher than 50% by weight to yield a filterable clear liquid, and upon termination of the reaction, filtering the reaction product and replacing the organic solvent by an oil or a mixture of oils chosen from natural oils and/or semisynthetic oils and/or synthetic oils.

6. A process according to claim 5, wherein, during the reaction, the organic solvent is evaporated off and recycled into the reaction mixture so as to produce therein a bubbling action which promotes the reaction.

7. A process according to claim 5 wherein the organic solvent used during the reaction is: (A) a nonpolar solvent chosen from naphtha, hexane, kerosene, benzene, toluene, xylene, or a mixture of paraffinic hydrocarbons of mineral or synthetic origin; or (B) a polar organic solvent chosen from 1-butanol, 2-butanol, ethylene glycol, propylene glycol, ethylene glycol monomethyl ether, ethylene glycol dimethyl ether, diethylene glycol and ethers thereof, mixtures of alcohols derived from paraffin, or methyl ethyl ketone.

8. A process according to claim 5, characterized in that the promoter for the fixation of carbon dioxide is methanol.

9. A process according to claim 7, wherein, during the reaction, the organic solvent is evaporated off and recycled into the reaction mixture so as to produce therein a bubbling action which promotes the reaction.

10. A process according to claim 6, wherein the promoter for the fixation of carbon dioxide is methanol.

11. A process according to claim 7, wherein the promoter for the fixation of carbon dioxide is methanol.

12. A process according to claim 10, wherein the promoter for the fixation of carbon dioxide is methanol.

13. Calcium soaps according to claim 2, wherein the oil consists essentially of at least one natural oil and/or at least one semisynthetic oil and/or at least one synthetic oil.

14. Calcium soaps according to claim 3, wherein the oil consists essentially of at least one natural oil and/or at least one semisynthetic oil and/or at least one synthetic oil.

15. A calcium soap according to claim 1, wherein said at least one hydrocarbyl carboxylic acid is a mixture of acids.

16. A calcium soap according to claim 15, wherein said at least one hydrocarbyl carboxylic acid contains not more than 11 carbons.

17. A calcium soap according to claim 1, wherein said at least one hydrocarbyl carboxylic acid is 3-methylhexanoic acid, isooctanoic acid, 4,5-dimethylhexanoic acid, isononanoic acid, 3,5,5-trimethylhexanoic acid, isodecanoic acid, 3-ethyloctanoic acid, isoundecanoic acid, or 4-ethylnonanoic acid.

18. A calcium soap according to claim 16, wherein said at least one hydrocarbyl carboxylic acid is a mixture of acids.

19. A calcium soap according to claim 17, wherein said at least one hydrocarbyl carboxylic acid is a mixture of acids.

20. A soap according to claim 4, said calcium being dissolved in 30–60% by weight of oil.

21. A soap according to claim 1, being a translucent solid.

22. A soap according to claim 1, being a translucent paste.

23. A soap according to claim 3, wherein the soap has a Total Basic Number of at least on the order of 500.

* * * * *